(12) United States Patent
Sundaresan et al.

(10) Patent No.: US 6,399,939 B1
(45) Date of Patent: Jun. 4, 2002

(54) SENSOR ARRAY SYSTEM

(75) Inventors: Mannur J. Sundaresan; Anindya Ghoshal, both of Greensboro; Mark J. Schulz, Summerfield, all of NC (US)

(73) Assignee: North Carolina A&T State University, Greensboro, NC (US)

( * ) Notice: Subject to any disclaimer, the term of this patent is extended or adjusted under 35 U.S.C. 154(b) by 0 days.

(21) Appl. No.: 09/592,884

(22) Filed: Jun. 13, 2000

(51) Int. Cl.[7] .................. G01N 21/00; G01N 29/00; G01H 1/00
(52) U.S. Cl. .................. 250/231.1; 73/587; 73/768; 73/DIG. 4
(58) Field of Search .................. 250/231.1, 227.14, 250/227.16; 73/587, 588, 628, 641, 649, 763, 768, 772, 774, 780, DIG. 4, 781, 786

(56) References Cited

U.S. PATENT DOCUMENTS

| | | | | |
|---|---|---|---|---|
| 3,787,700 A | * | 1/1974 | Chassen | 250/559.25 |
| 5,932,807 A | * | 8/1999 | Mallart | 73/641 |
| 6,076,405 A | * | 6/2000 | Schoess | 72/587 |

OTHER PUBLICATIONS

Life management of aging air force aircraft: NDE prespective; article from Air Force Wright Laboratory; vol. 2455; undated.
Ultrasonic imaging for corrosion and fatigue cracks in multilayered airplace structures; article from Center for Quality Engineering and failure Prevention; vol. 2945; undated.
Acoustic Emission Sensing Using Piezoceramic and Active Fiber Composite Patches; article from University of Missouri; undated.
ICCE/6; Damage Detection Using A Layer Vibrometer and Active Fiber Composite Patch; 1999.
UNSW; Composites in the Transportation Industry; Feb. 2000.
Article entitled Active Composite Materials and Damage Monitoring; undated.
Article entitled Piezoelectric Fiber Composites wih Interdigitated Electrodes; Journal of Intelligent Material Systems and Structures, vol. 8, Oct. 1998.

(List continued on next page.)

Primary Examiner—Stephone Allen
(74) Attorney, Agent, or Firm—MacCord Mason PLLC (57) ABSTRACT

A sensor array for nondestructively monitoring a structure to detect a critical event. The sensor array includes a plurality of discrete sensor nodes, each of the discrete sensor nodes producing an electrical signal in response to a structural event. In the preferred embodiment, the sensor nodes include a plurality of piezoceramic fibers arranged in a planar array in which the fibers are aligned substantially parallel to each other, each of the fibers having a plurality of polarized regions that are substantially oriented according to their polarity in either a series, parallel, or combined arrangement of series and parallel orientations, and an electrical interface connecting the plurality of polarized regions of each fiber in series with one another. A signal adder receives and combines the electrical signals from each of the discrete sensor nodes to form a single sensor array output signal. In the preferred embodiment, the electrical interface further includes at least one electrical bus substantially aligned with the fibers and a signal processing module for receiving and processing the single sensor output signal. The signal processing module is linked through the digital data bus to a central processing unit. The plurality of discrete sensor nodes may further be divided into discrete subgroups, each located at a different structural location to provide a degree of sensing and determining the location of the structural event. In the preferred embodiment, the discrete sensor nodes are electrically connected in series, thereby forming a continuous series connection between each of the discrete sensor nodes to improve the likelihood that a critical structural event will be detected.

35 Claims, 9 Drawing Sheets

OTHER PUBLICATIONS

Article entitled Residual Stiffness and Actuation Properties of Peizoelectric Composites: Theory and Experiment from Journal of Intelligent Material Systems and Structures, vol. 9—Sep. 1997.

A Review on the Modelling of Piezoelectric Sensors and Actuators Incorporated in Intelligent Structures from the Journal of Intelligent Material Systems and Structures, vol. 9—Jan. 1998.

Continuum, An innovative provider of piezoelectric components and integrated systems for motion contril, and vibration suppression; 1999.

CeraNova Corporation; Active Composites for Smart Structures; copyright 2000.

ACX (Active Control eXperts); information from the internet; copyright 1996–2000.

Article entitled Active Damage Interrogation System for Structual Health Monitoring; SPIE vol. 3044, undated.

Article entitled Structual Frequency Response Function Acquisition Via Electric Impedance Measurement of Surface–Bonded Piezoelectric Sensor/Actuator from the American Institute of Aeronautics and Astronautics; copyright 1995.

Rotor Acoustic Monitoring System (RAMS)—A Fatigue Crack Detection System; May 1997.

Advanced, Waveform Based Acoustic Emission Detection of Matrix Cracking in Composites; Materials Evaluation, vol. 53(9), 09/95.

Article entitled Acoustic Emission Structual Health Monitoring; Dec. 1998.

The Use of AET for Classifying Failure Modes in Composite Materials; Dec. 1993.

Implementation of a Real–Time Impact Identification Technique for Stiffened Composite Panels; Dept. of Aeronautics and Astronautics, Stanford University.

Built–In Diagnostics for Impact Damage Identification of Composite Structures; Stanford University; undated.

Tech Briefs, vol. 23, No. 10 from NASA, Oct. 1999.

* cited by examiner

SENSOR ARRAY SYSTEM

BACKGROUND OF THE INVENTION

(1) Field of the Invention

The present invention relates generally to non-destructive testing. More particularly, the present invention relates to a sensor array system for structural monitoring in which the sensors are arranged in a continuous series connection for increasing the likelihood of detecting a critical event.

(2) Description of the Prior Art

The performance of modem-day military helicopters, missiles, tanks, aircraft, and other static or dynamic structures is critically dependent on the reliability of advanced composite materials and heterogeneous armor materials. There has been a reluctance to deploy such high performance materials in critical structural applications because of their susceptibility to in-service damage. The damage occurring in these materials may be difficult to track and can propagate quickly during operation of the vehicle or structure, resulting in the loss of the entire vehicle.

Conventional non-destructive evaluation techniques are labor intensive, expensive, error prone, and unworkable for efficient integration into composite and heterogeneous structures. Autonomous integrated Structural Health Monitoring (SHM) techniques are a revolutionary concept in the maintenance of structures. SHM techniques continuously monitor the condition of a stricture. Various approaches for SHM under development use piezoceramic sensors and actuators that require separate wiring connections for each sensor and actuator element, storage of pre-damage data for each sensor, and instrumentation for active generation and sensing of diagnostic signals. When the structural geometry is complex—e.g., either the structure has varying thickness, curvature, ribs, joints, or heterogeneous materials, or damage is located near boundaries of the structure—it becomes difficult to detect small damage using SHM methods. In addition, the number of sensor circuits and computations required increases the overall complexity and cost of the structure.

One approach to this problem is to integrate many fiber-optic strain gauges directly within the structural material. An optical fiber with twenty or more Bragg gratings can measure static and dynamic strains at discrete locations on the structure. An optical analyzer can multiplex over each fiber and each grating to measure strains at a large number of points on a structure. This approach is being implemented on bridges, pressure tanks and other structures. However, fiber optic sensors have limitations when applied to monitoring complex composite structures where damage can occur anywhere on the structure and in any direction. For example, discrete strain measurements can miss damage because the measurement is very localized at the fiber/grating. In addition, an optical analyzer using multiplexing and multiple connections is expensive; measurements are not simultaneous and the frequency bandwidth may be too low to sense Acoustic Emission (AE) signals.

AE sensors are presently suitable for detection of damage at "hot spots. " The use of AE measurements for SHM of large structures may have certain advantages since it is a passive sensing technique. Passive sensing methods are simpler and may be more practical than using active interrogation methods. However, present passive acoustic emission and monitoring techniques require bulky instrumentation with numerous channels, long connections, and centralized data analysis. It may be impractical to embed these systems on the structure to operate in the field. Another limitation is that AE waveforms from such sensors are too complicated for purposes of source characterization.

Thus, there remains a need for a new and improved sensor array system for structural health monitoring that will provide sufficient spatial coverage to efficiently sense AE signals and, at the same time, is simple and cost effective.

SUMMARY OF THE INVENTION

The present invention is directed to a sensor array for non destructively monitoring a structure to detect a critical event. The sensor array includes a plurality of discrete sensor nodes, each of which produces an electrical signal in response to a structural event. The sensor nodes may include either a piezoceramic (PZT) wafer, a plurality of piezoceramic fibers, accelerometers, or chemical sensors arranged in either a planar or three dimensional array. In the preferred embodiment, the sensor nodes include a plurality of piezoceramic fibers. The fibers are aligned substantially parallel to each other within the sensor node and are electroded and poled to act as a single sensor node. The fibers have a plurality of polarized regions that are substantially oriented in series according to their polarity in a +–+–+– . . . arrangement, or, alternatively, in parallel with each other. An adding circuit connects the plurality of polarized regions in series with one another. A signal adder receives and combines the electrical signals from each of the discrete sensor nodes to form a single sensor array output signal.

In the preferred embodiment, the electrical interface further includes at least one electrical bus substantially aligned with the fibers and a signal processing module for receiving and processing the single sensor output signal. The signal processing module includes an input connected to the signal adder, an impedance matching amplifier connected to the input for amplifying the single sensor output signal, and an output. The signal processing module may further include an electronic noise filter.

In addition, the sensor array may further include an electronic trigger for detecting the beginning of an event and providing a trigger signal and a display, such as an oscilloscope, connected to the trigger and the output, whereby the trigger signal activates the display for observing the output.

The sensor array also may further include a threshold detector for detecting an output exceeding a predetermined threshold level and providing an alarm signal when the output exceeds the predetermined threshold level.

The plurality of discrete sensor nodes may further be divided into discrete subgroups, termed unit cells, each located at a different structural location. For example, a subgroup could be part of each rotor blade of a helicopter or different armor panels of a tank to provide a degree of sensing the location of the structural event in a specific element of the structure.

In the preferred embodiment, the discrete sensor nodes in one or more subgroups are electrically connected in series, thereby forming a continuous series connection between each of the discrete sensor nodes to improve the likelihood that a critical structural event will be detected.

Accordingly, one aspect of the present invention is to provide a sensor array for nondestructively monitoring a structure to detect a critical event. The sensor array includes a plurality of discrete sensor nodes in which each of the discrete sensor nodes produces an electrical signal in response to a structural event, and a signal adder for receiving and combining the electrical signals from each of the discrete sensor nodes to form a single sensor array output signal.

Another aspect of the present invention is to provide a sensor for nondestructively monitoring a critical event. The sensor includes: at least one sensing node having a plurality of piezoceramic fibers arranged in a planar array in which the fibers are aligned substantially parallel to each other within the sensing node, wherein each of the fibers has a plurality of polarized regions that are substantially oriented in series according to their polarity in a predetermined arrangement; and an electrical interface connecting the plurality of polarized regions of each sensor node in series with one another.

Still another aspect of the present invention is to provide a sensor array for nondestructively monitoring a structure to detect a critical event. The sensor array includes: a plurality of discrete sensor nodes in which each of the discrete sensor nodes produces an electrical signal in response to a structural event, wherein the sensor nodes include a plurality of piezoceramic fibers arranged in a planar array in which the fibers are aligned substantially parallel to each other, each of the fibers has a plurality of polarized regions that are substantially oriented according to their polarity in a predetermined arrangement; an electrical interface connecting the plurality of polarized regions of each fiber in series with one another; and a signal adder for receiving and combining the electrical signals from each of the discrete sensor nodes to form a single sensor array output signal.

These and other aspects of the present invention will become apparent to those skilled in the art after a reading of the following description of the preferred embodiment when considered with the drawings.

DESCRIPTION OF THE PREFERRED EMBODIMENTS

In the following description, like reference characters designate like or corresponding parts throughout the several views. Also in the following description, it is to be understood that such terms as "forward, " "rearward, " "left, " "right," "upwardly, " "downwardly, " and the like are words of convenience and are not to be construed as limiting terms.

Figure 1:
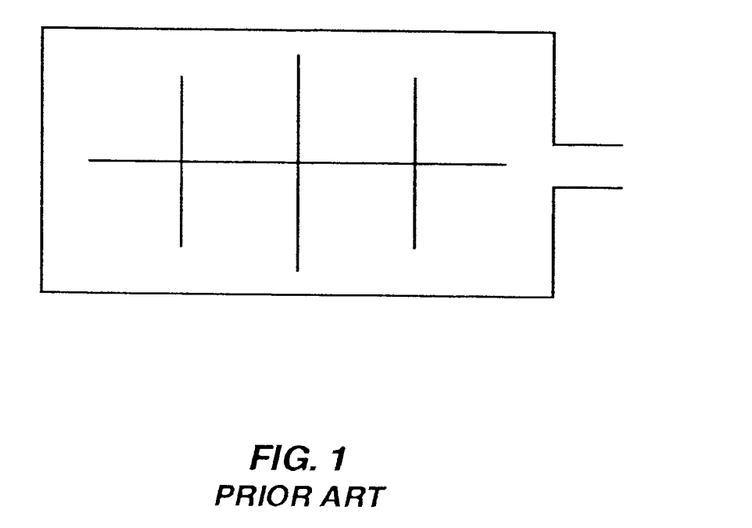
FIG. 1 is a top elevation view of a prior art, bi-directional/single node PZT wafer sensor.
Figure 2:
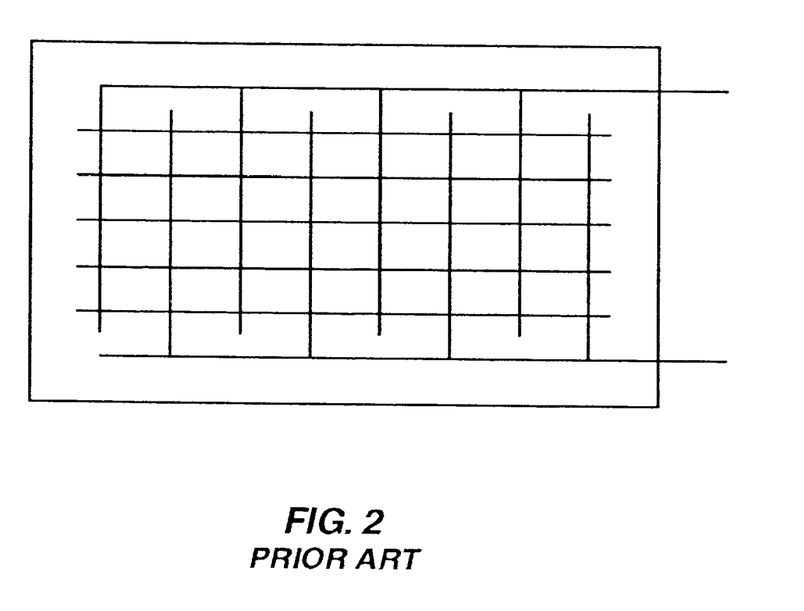
FIG. 2 is a top elevation view of a prior art, uni-directional/single node PZT fiber sensor.
Figure 3:
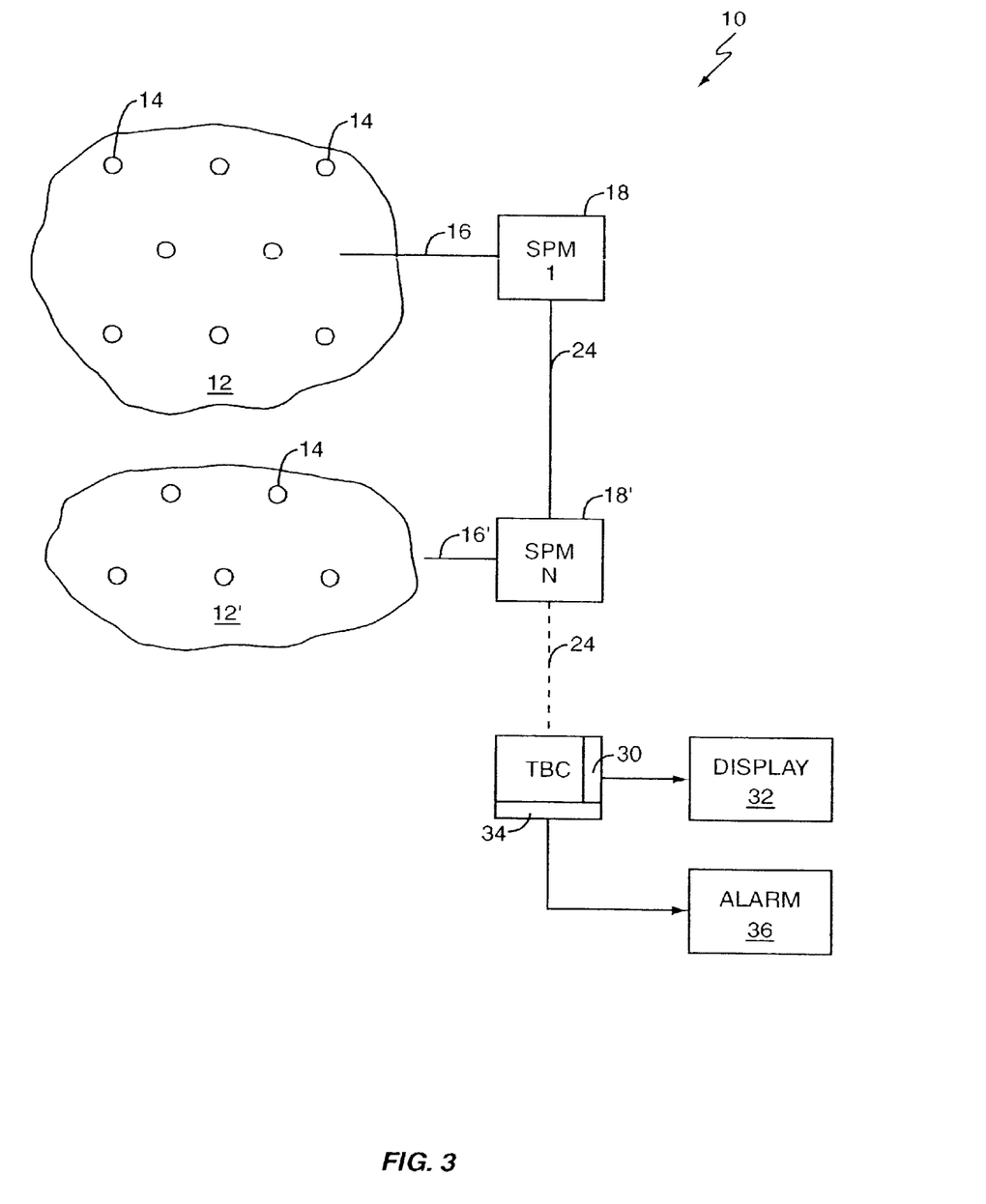
FIG. 3 is a block diagram of a sensor array including a plurality of discrete sensor nodes combined into a single output constructed according to the resent invention.

Referring now to the drawings in general and FIG. 3 in particular, it will be understood that the illustrations are for the purpose of describing a preferred embodiment of the invention and are not intended to limit the invention thereto. As best seen in FIG. 3, a sensor array, generally designated 10, is shown constructed according to the present invention. The sensor array 10 includes three major sub-assemblies: a plurality of discrete sensor nodes 14; a signal adder for combining the output of each of the discrete sensor nodes 14 into a single output 16; and at least one signal processing module 18. Similar signal processing units are commercially available. Among the manufacturers of such units is Endevco Corporation, located in San Juan Capistrano, Calif.

Figure 4:
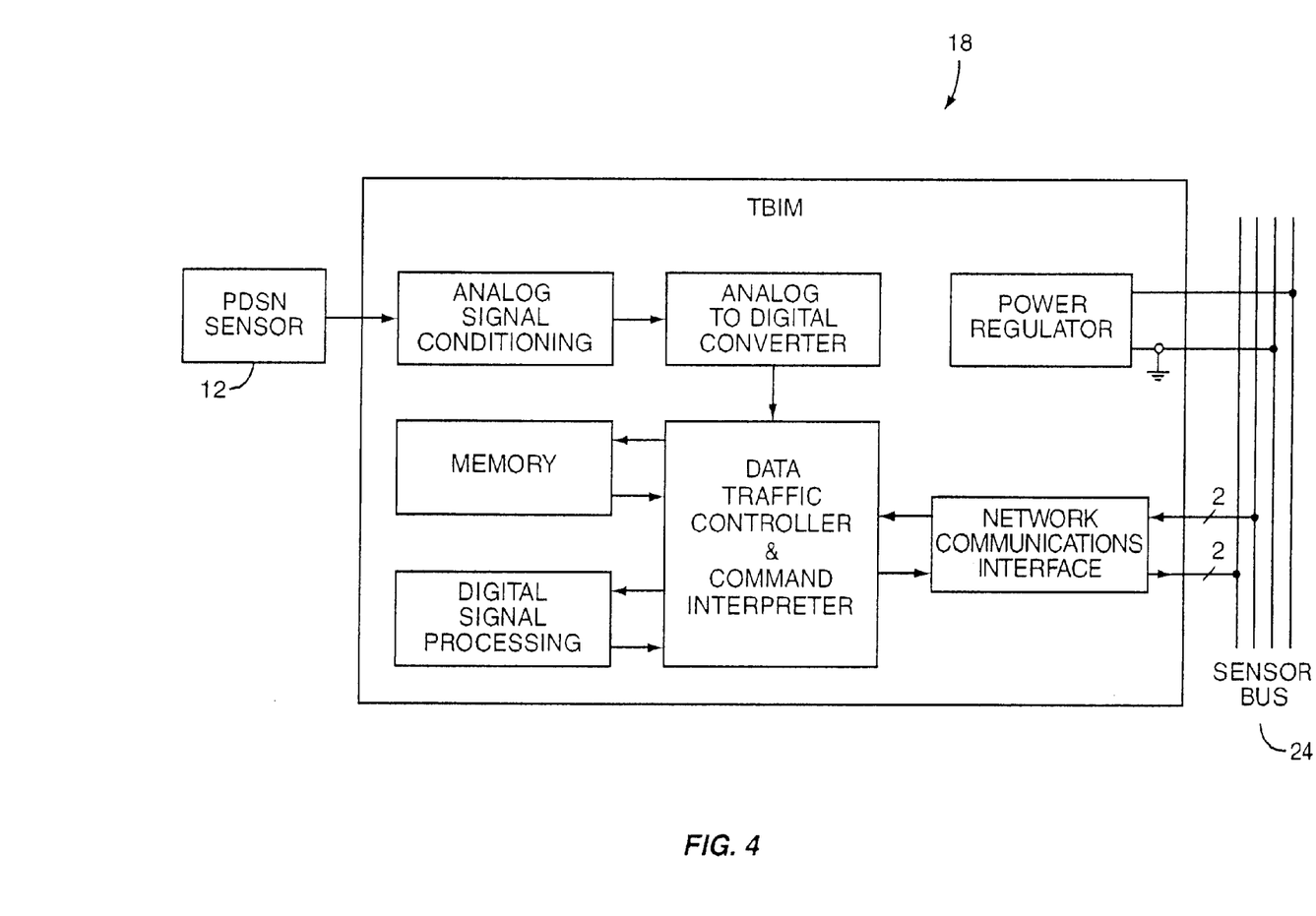
FIG. 4 is a enlarged block diagram of the signal processing module for the sensor array shown in FIG. 3.

As best seen in FIG. 4, an embedded electronic signal processing module 18 conditions the AE signal and performs the data processing. The signal processing module 18 itself is made of an analog ASIC (Application Specific Integrated Circuit), for analog signal conditioning, and a digital ASIC which performs the quantification, pattern recognition, timing, and short time data storage.

As best seen in FIG. 3, a digital data bus 24 provides communication between the signal processing modules 18 and the CPU 30. Further, this bus also powers the signal processing modules 18. The Transducer Bus Controller (TBC) is located in the CPU 30.

The CPU 30 assembles the processed information sent by the sensor nodes 14, and assesses any damage growth that may be occurring in the structure. A special feature of the present invention is that the acoustic emission data processing takes place within the respective signal processing modules 18, and only the processed information is communicated outward through the interface bus 24. Furthermore, the fibers are connected in either series, parallel, or a combined series/parallel configuration to tailor the sensitivity of the sensor nodes 14 and match the environmental conditions under which it is operating. Bi-directional communication between the signal processing modules 18 and the CPU 30 takes place over the single digital data bus 24, thus eliminating cumbersome cables.

In operation, the CPU 30 initializes all sensor nodes 14, including their short term clocks. The CPU 30 then queries each sensor node at time intervals of the order of a few tens of seconds to download the gathered information. The signal processing modules 18 and the sensor nodes 14 perform the digitization and analysis of the AE signals and store in a tabular form within its memory only those processed data that are recognized as related to damage growth for uploading to the CPU 30.

Among the parameters stored in the signal processing modules 18 are the time of occurrence of the AE event, energy content of the AE event, and the amplitude, duration, pattern, and other relevant parameters of the AE signal envelope. The TBC addresses each signal processing module 18 sequentially to upload the processed information from the signal processing modules 18, 18' permanently stored in CPU 30.

Figure 5:
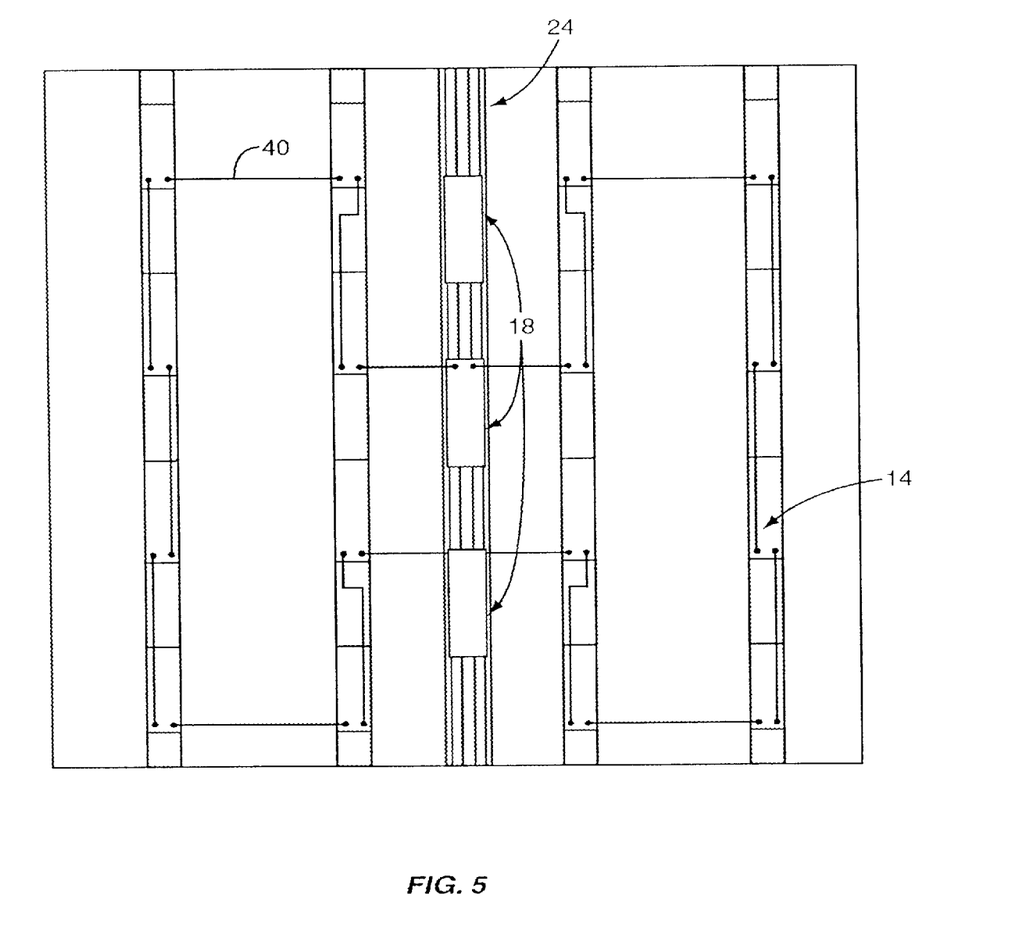
FIG. 5 is a top elevation view of the PZT fiber sensor array having a plurality of discrete sensor nodes connected in series and combined into a single output constructed according to the present invention.

As best seen in FIG. 5, the collection of sensor nodes 14 forms a unit cell of a 'smart' composite material. The sensor array 10 can be constructed by embedding tens or hundreds of these sensor nodes 14 in laminated composite or textile composite structures. In the preferred embodiment, each of these sensor nodes 14 is formed from piezoceramic tapes whose segments act as independent sensor nodes 14 that detect damage to the structure by measuring AE waves generated by cracks in the material or breakage of fibers. The piezoceramic fibers can also potentially measure dynamic strains within the structure, which is useful for monitoring and regulating load paths within the structure to extend its safe life.

Active Fiber Composite (AFC) materials using PZT fibers (developed at MIT and commercialized by Continuum Control Corporation, Billerica Mass.) or ribbons (recently developed by CeraNova Corporation, Franklin Mass.) are preferably used to construct long continuous sensors. Interdigitated (IDT) electrodes are used to pole and electrically connect the sensor. The AFC is thermally stable, has a long fatigue life, provides great flexibility in tailoring and designing a sensor material, and is strong and rugged enough to be used on helicopters, in armor, and in layered composites. Because labor comprises most of the cost of producing the sensor tape, the use of a single ribbon effectively replaces six circular fibers while still retaining the advantages of the fibers, and significantly reduces the cost of the distributed sensors.

Overall, the combination of fine piezoceramic fibers or ribbons with a flexible matrix provides a sensor material that is more robust and has a higher ultimate strain than the monolithic ceramics. The use of fibers or ribbons retains most of the stiffness of monolithic piezoceramic patches, and the unidirectional alignment creates the desired sensing/actuation in a single direction. The active fibers and structural fibers can be mixed within a single ply or can form separate plies in a composite. The overall laminate properties are found by a layer-wise integration of the constitutive equations for the layers. These properties are used in wave propagation simulations to determine the dynamic response of the sensor composite.

The electrode configuration can be designed to pole the fibers axially or through their thickness. Thin foil conductors (IDT electrodes) oriented perpendicular to the fibers are used on the top and bottom of the fibers. The conductors are used both for electroding and poling. The advantages of these designs are: (a) if the sensor is poled through the thickness of the fibers, the electrodes are easy to manufacture; (b) non-conductive structural fibers can be mixed with the sensor fibers, or conductive fibers can be put in adjoining layers; (c) the sensor can measure dynamic strains above 0.5 Hz.; (d) the sensor can be one cell of the system and AEs can be detected from all segments simultaneously; (e) the electrodes are deposited directly on the active fiber for ease of manufacturing and to allow a higher signal output when operating in the low field range; (f) ribbons which are larger than fibers and easier to fabricate can be used instead of fibers, making electroding easier and polarization more uniform; and (g) once encapsulated in a matrix, the ribbon can be woven as a straight fiber into textile composites. Both transverse and axial poling concepts are possible. In conventional AFCs, the electrodes are placed on the matrix above the fibers to prevent concentrations of the electric field in the fiber that can lead to locally high strains and fiber breakage. Because the fibers are used for sensing and not actuation, fatigue due to high electric field concentrations that normally necessitates use of the electroding above the fibers is absent. The electrodes are used for directly poling the sensor material.

Figure 6:
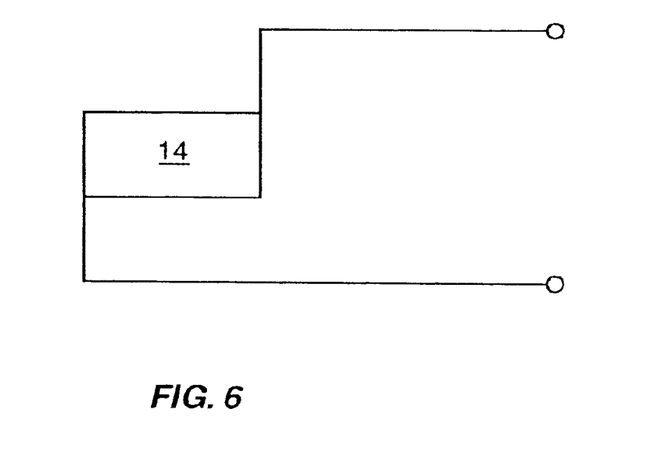
FIG. 6 is a simplified schematic of the bi-directional/single node PZT wafer sensor of the prior art, and the prior-art uni-directional/single node PZT fiber sensor shown in FIGS. 1 and 2.
Figure 7:
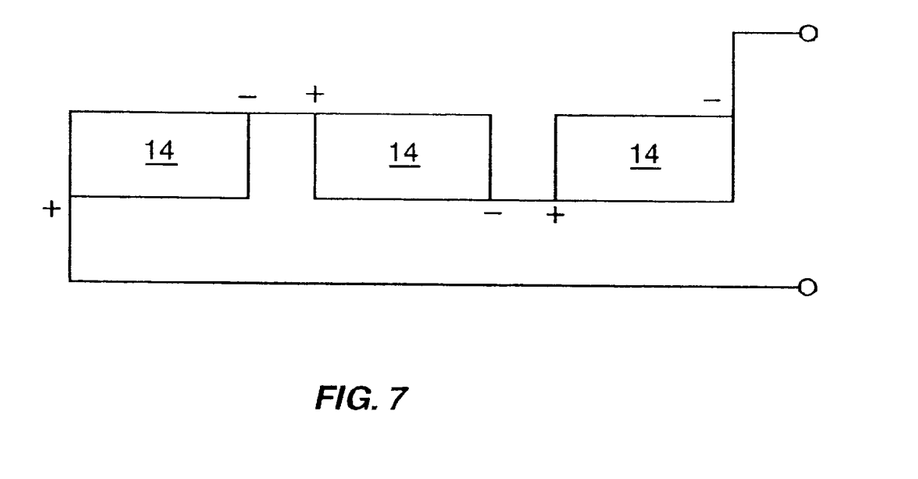
FIG. 7 is a simplified schematic of the sensor array shown in FIG. 5 that includes a plurality of discrete sensor nodes combined into a single output constructed according to the present invention.

As best seen in FIG. 6 (the prior air) and FIG. 7 (the present invention), the initial modeling that was performed to study the composite couples the elastic equations of a bar or plate structure to the piezoelectric constitutive equations and a parallel tuning electric circuit.

The piezoelectric equations to model a PZT or AFC sensor are:

$$\begin{bmatrix} D \\ T \end{bmatrix} = \begin{bmatrix} \varepsilon^S & e \\ -(e)^t & c^E \end{bmatrix} \begin{bmatrix} E \\ S \end{bmatrix} \quad (1)$$

where D is the electric displacement in coulombs/m$^2$, T is the stress in N/m$^2$, E is the electric field in volts/m, S is the strain, $\in^S$ is the clamped dielectric in Farads/m, e is the induced stress constant in Coluomb/m^2 or equivalently N/(m*volt), t is transpose, and $c^E$ is the constant field stiffness in N/m$^2$.

Considering a single axis, the equations in (1) are represented as:

$$D_j = \left(\varepsilon^S E(t) + e\frac{\partial w(x_j, t)}{\partial x}\right)\text{sgn}(j) \quad (2)$$

$$i_{gj} = \left[C_j \dot{V}_o/K + e\frac{\partial^2 w(x_i, t)}{\partial x \partial t}\right] A_c \text{sgn}(j) \quad (3)$$

where j represents the jth segment of the sensor, w is the longitudinal displacement, V is the voltage, C is the capacitance of the piezoceramic, and the sgn function allows connection of the segments with positive or negative polarities. An electric circuit representing equations (2–3) for series connectivity is shown in FIG. 7.

An electrical parallel tuning circuit is connected to the acoustic emission sensor circuit to filter out the ambient vibration response to more accurately sense the acoustic emissions from cracks.

The combined equations for the electrical model of the AFC sensor and the connected tuning circuit are:

$$\begin{bmatrix} L_s & 0 \\ -L_p & L_p \end{bmatrix} \begin{bmatrix} \dot{i}_l \\ \dot{i}_s \end{bmatrix} + \begin{bmatrix} L_p/(R_p N C_p) & 0 \\ 0 & R_s \end{bmatrix} \begin{bmatrix} i_l \\ i_s \end{bmatrix} + \quad (4)$$

$$\begin{bmatrix} 1/(NC_p) & 1/(NC_p) \\ 0 & 1/C_s \end{bmatrix} \begin{bmatrix} i_l \\ i_s \end{bmatrix} = -\frac{A_e e}{NC_p} \begin{bmatrix} \sum_{j=1}^{ns} w_{xt}^j \text{sgn}(j) \\ 0 \end{bmatrix}$$

where is and il are the currents in the tuning circuit, R, L, CS are the circuit parameters, $C_p$, $A_e$, e are the sensor piezoceramic material parameters, and N, $w^j_{xt}$, sgn(j) are the number of sensor nodes, the strain rate at node j, and sign of the connectivity of node j.

An elastic model of a bar or plate is used to simulate the response of the sensor material subjected to AE or other excitation. The plate with the segments is shown in FIG. 9. The segments S1, S2, S3, S4, . . . S16 model the sixteen sensor segments of one fiber tape in the composite shown in FIG. 3. Since the AFC is poled using the electrodes, each segment acts as a uniform sensor. The segments can be spaced and connected in alternating polarity to cancel low frequency (<100 KHz) structural vibrations and the length of the segments can be matched to the half wavelength of the dominant stress waves to be measured.

This approach uses the continuous nature of the sensor as a spatial filter to cut-off the low frequency response that masks the AE response. If small segments are used, the continuous sensor can be designed similar to an acoustic wave filter to measure Lamb waves produced from damage propagation. Organic composites produce extensive AEs in the presence of damage. Thus, monitoring of AE in composites can be used as a passive method for damage detection. AEs in thin composite structures propagate as Lamb or plate waves. The two plate modes of AE waves observed in AE signals are the symmetrical, or extensional, wave and the anti-symmetrical, or flexural, mode. Extensional plate waves contain higher frequency components and occur first in the signal, whereas the flexural waves contain lower frequency components, have higher amplitudes, and occur later in the wave. The extensional waves are non-dispersive (i.e., the wave velocity is independent of the wave number) and these plate waves can travel longer distances than dispersive waves. The flexural waves, on the other hand, are dispersive in nature and damage is more difficult to detect using these waves because the phase velocity and amplitudes change with temperature and small variations in boundary conditions.

Figure 8A:
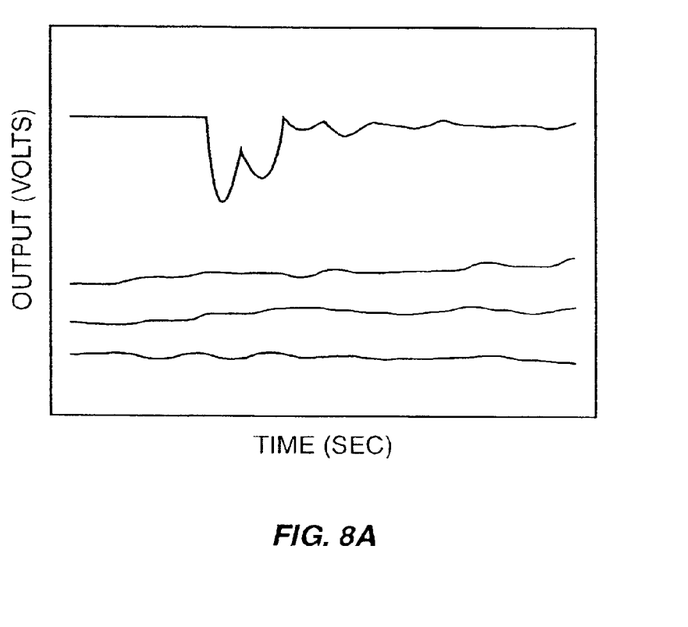
FIGS. 8A and 8B are graphs illustrating the effect of adding a plurality of discrete sensor node outputs into a single output.
Figure 8B:
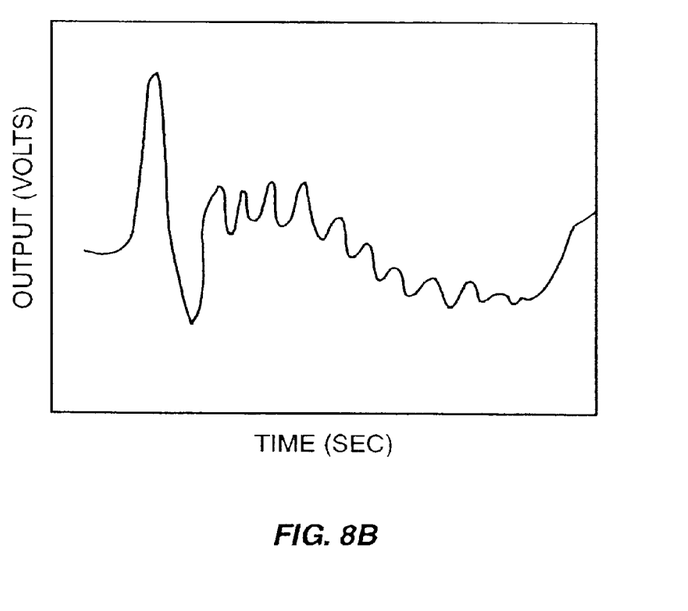

As best seen in FIGS. 8A and 8B, experiments have been performed to verify the characteristics and potential of the continuous sensor material. An AE event was simulated by breaking a pencil lead near sensor 1, and AE waveforms corresponding to four sensors were recorded using a digital oscilloscope, as shown in FIG. 8A. Sensor 1, which was nearest to the simulated AE source, registered the highest signal magnitude, and, more significantly, had higher frequency components present in the signal. Sensors 2, 3 and 4 had progressively fewer high frequency components in the signal, because high frequency components attenuate as a function of distance traveled more rapidly than low frequency components. Frequency components above 100 kHz were almost totally absent in these three sensors.

In practice, frequency components that are higher than 100 kHz can provide valuable information about the AE source. Obtaining those frequency components, however, would require a large number of AE sensors to monitor most structures. The weight, cost, and complexity of such a multi-channel instrument may be prohibitive.

Next, a distributed sensor was formed by connecting the four sensors to a single channel of a digital oscilloscope. A signal was generated by breaking a pencil lead near sensor 1. The signal detected from this arrangement is shown in FIG. 8B. The response of the continuous sensor was reduced in amplitude, but the high frequency components were preserved intact and the amplitude levels were still adequate for AE sensing. In this experiment, the optimal circuit design was not used. Had the optimal design been used, it would have increased the voltage output of the continuous sensor to be equal or greater than the output of a single sensor near the pencil lead break. In addition, smaller sensors would be used in practice.

Figure 9A:
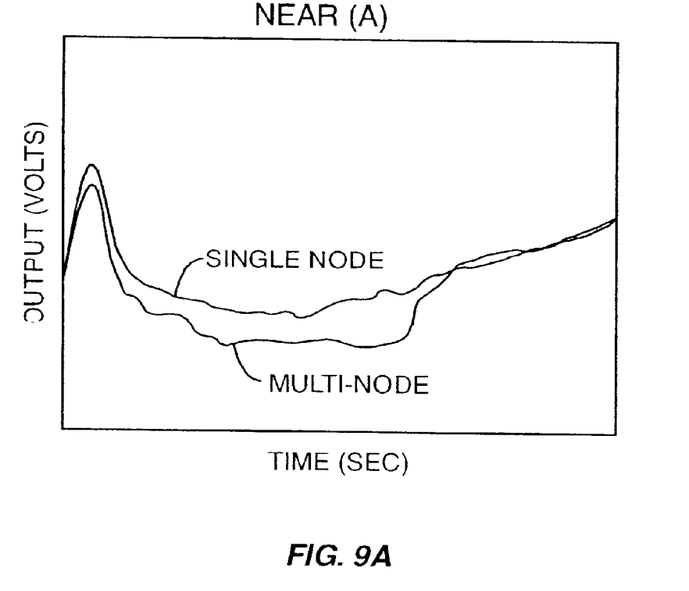
FIGS. 9A and 9B are graphs illustrating the difference between the response of a conventional single node sensor and the response of a multi-node sensor, and their dependence on the location of the structural event.
Figure 9B:
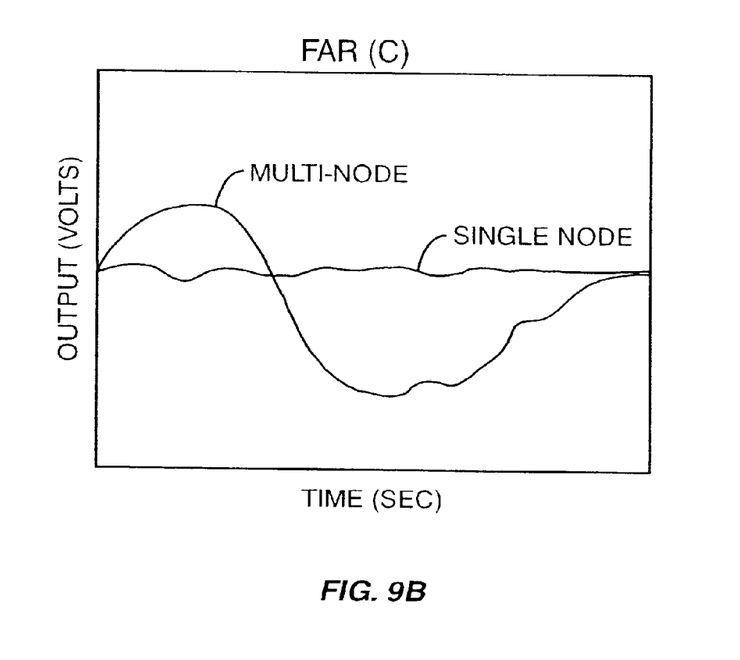
Figure 9C:
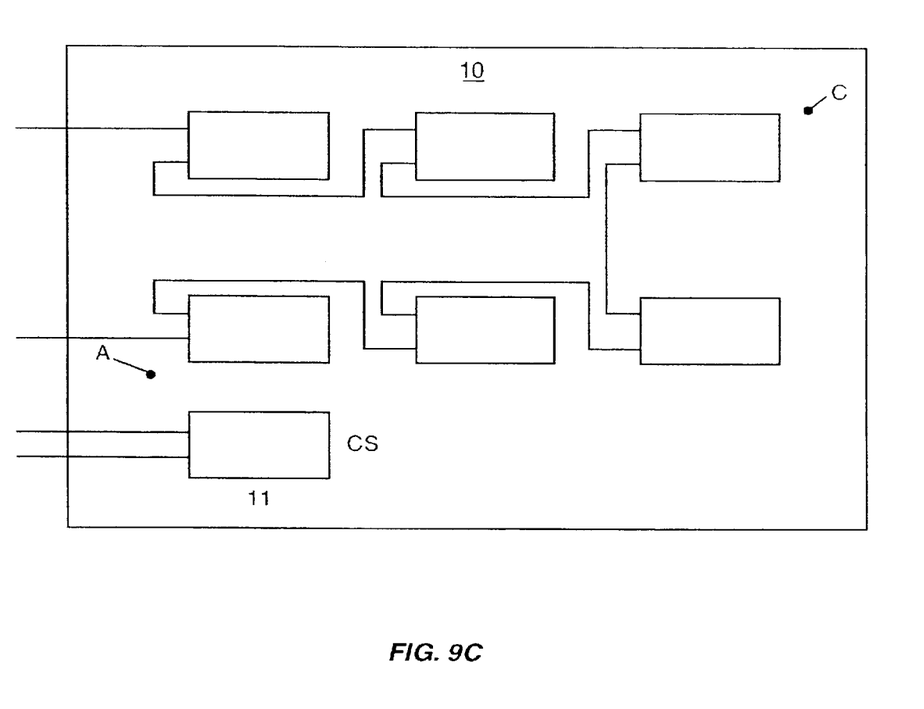
FIG. 9C is a schematic diagram showing the positions of a sensor array of the present invention and a single sensor relative to acoustic emission events.
Figure 10:
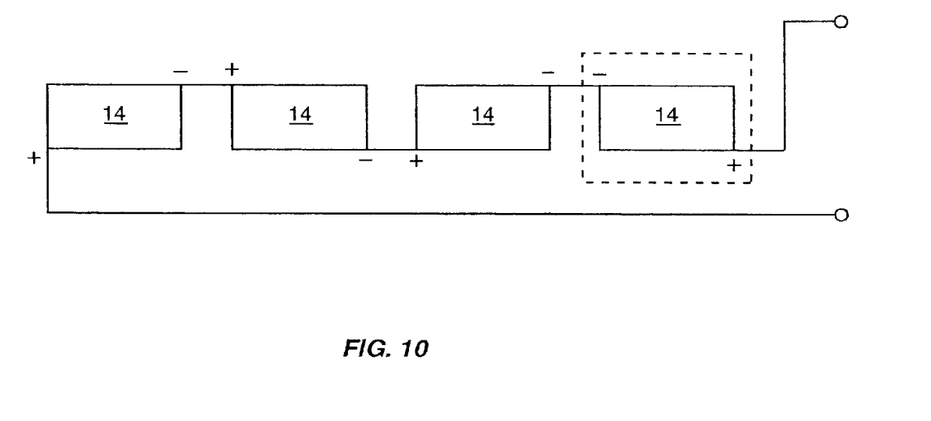
FIG. 10 is a simplified schematic of an alternative embodiment of the sensor array constructed according to the present invention as shown in FIG. 5, including a plurality of discrete sensor nodes combined into a single output.

As best seen in FIGS. 9A and 9B, the output of a continuous sensor array 10 was compared to that of a single PZT sensor 11 for detecting an acoustic emission on a fiberglass panel, shown in FIG. 9C. A pencil lead break at location A in FIG. 9C is detected by both the continuous sensor array 10 and the conventional sensor 11. In contrast, the sensor response due to a pencil lead break at location C in FIG. 9C shows that the continuous sensor array 10 captures the signal while the conventional sensor 11 at CS cannot sense an AE signal that is originating at a point distant from the sensor.

In operation, the continuous highly distributed sensor system can monitor entire structures with a single digital data bus 24 and can thus eliminate the bulky coaxial cables and greatly reduce the hardware and communication needs for a field deployable health monitoring system. To illustrate this, consider an AE event occurring at a random location along a straight-line segment of length L, while this segment is monitored through N equally spaced AE sensors. The maximum distance that the AE signal travels to reach the closest sensor is d=L/(2N). The number of sensors required would be determined by the exponential rate of attenuation of AE voltage signals given by $V=A_o e^{-Kd}/N^a$ where $A_o$ is a signal amplitude coefficient, a is an exponent, and K is a material-dependent decay constants The sensor array of the present invention is able to minimize the exponents d and a in the above equation, thereby maximizing the possibility of detecting an acoustic event.

In order to train the sensor network, a procedure of calibrating each unit cell can be established. Although the different unit cells attached to a structure may be similar to each other, the dynamics and wave propagation characteristics may vary from point-to-point on the structure. Unless each signal processing module takes these differences into account when reducing the data, errors can be introduced in the quantification of the AE activity. The calibration procedure could establish the threshold levels, data acquisition time window, and other related parameters.

Finally, the software in the CPU 30 will be robust enough to identify the failure of a sensor or signal processing module 18. Redundancy can be built into the sensor network, such that most damages will be detected by more than one unit cell.

Among the advantages provided by the sensor array 10 of the present invention are: (i) a drastic reduction of the weight, cost, and complexity of instrumentation; (ii) increased probability of detection of the acoustical event due to the reduction in the source-to-sensor distance; and (iii) a more faithful retention of the acoustical signature, including the high frequency components, of the source event in the signal transmitted from the distributed sensor, due to minimization of the source-to-sensor distance.

Since the high frequency components of an AE signal attenuate much faster than the low frequency components, the signal from the sensors will have little resemblance to the source event if the travel distance d is long. Conventional AE techniques quickly become impractical for most field-deployable health monitoring applications, as they require as many independent data acquisition channels as the number of sensors.

With the active composite continuous sensor of the present invention, an entire structure can be monitored by a group of continuous sensors or unit cells with N sensing elements, all connected to a single digital data acquisition bus. By increasing the number of sensor elements, it is possible to have access to the leading edge of the AE waveform before it is dispersed. Such access is crucial in identifying the source mechanisms and estimating the source magnitude. The AE source can be located within the region of a given distributed sensor and network algorithms will be developed to locate the damage more precisely for subsequent closer inspection and repair.

Certain modifications and improvements will occur to those skilled in the art upon a reading of the foregoing description. By way of example, the electrode pattern—specifically, the width and spacing of the AFC sensor segments—can be designed to optimize the voltage and current output of the sensor for a particular application.

Transverse electroding and poling can be used instead of interdigital electrodes and can simplify the design and reduce the cost of the AFC sensor segments.

The continuous sensor segments of the present invention can also be connected in four possible combinations to tailor the sensor characteristics, such as signal level and spatial filtering, for specific applications. The four combinations are: (i) an aligned series connection—i.e., (+−)(+−)(+−)(+−) . . . ; (ii) an alternating series connection—i.e., (+−)(−+)(+−)(−+) . . . ; (iii) an aligned parallel connection in which all positive terminals are connected to a common positive point and all negative terminals to a separate, common negative point; and (iv) an alternating parallel connection in which the parallel connection for the adjacent sensor nodes are reversed.

Besides acoustic emissions, the sensor array of the present invention can measure different events—including peak strains, peak vibration levels, and stress wave propagation from impacts on the structure—that are pertinent to structural health monitoring. The large area coverage and simultaneous sensing can localize the event to a particular unit cell. The sensor array can be configured for integration into composite materials or attachment to the surface of metallic structures such as an aircraft. By having segments of the sensor array connected with different directional sensitivity, the unidirectionality of the active fiber composite sensor material can also be used to determine the location of events.

The individual sensor elements or nodes may also include an addressable switch that can be used to include or exclude that sensor element from the network of sensor thus providing a self-configuring continuous sensor that can automatically adapt to operating conditions. The local processor can have the ability to address the switch and to configure the network of sensors to be employed at a given stage to monitor structure health. Communication between the local processor and the individual sensor nodes is established by either a local digital data bus or the signal leads.

It should be understood that all such modifications and improvements have been deleted herein for the sake of conciseness and readability but are properly within the scope of the following claims.

We claim:

1. A sensor array for nondestructively monitoring a structure and to detect a critical event, said sensor array comprising:
   (a) a plurality of discrete sensor nodes, each of said discrete sensor nodes producing an electrical signal in response to a structural event; and
   (b) a signal adder electrically connected to said plurality of discrete sensor nodes, said signal adder being capable of receiving and combining said electrical signal from each of said discrete sensor nodes to form a single sensor array output signal.

2. The sensor array of claim 1, further including a signal processing module for receiving and processing said single sensor output signal.

3. The sensor array of claim 2, wherein said signal processing module includes an input connected to said signal adder, an impedance matching amplifier connected to said input for amplifying said single sensor output signal, and an output.

4. The sensor array of claim 3, further including an electronic trigger for detecting the beginning of an event and providing a trigger signal.

5. The sensor array of claim 4, further including a display connected to said trigger and to said output, whereby said trigger signal activates said display for observing said output.

6. The sensor array of claim 5, wherein said display is an oscilloscope.

7. The sensor array of claim 3, further including a threshold detector for detecting an output exceeding a predetemined threshold level and providing an alarm signal.

8. The sensor array of claim 7, further including an alarm connected to said threshold detector whereby said alarm is actuated when said output exceeds said predetermined threshold level.

9. The sensor array of claim 3, wherein said signal processing module further includes an electronic noise filter.

10. The sensor array of claim 1, wherein said plurality of discrete sensor nodes is further divided into discrete subgroups, each located at a different structural location.

11. The sensor array of claim 1, wherein said discrete sensor nodes are electrically connected in series, thereby forming a continuous series connection between each of said discrete sensor nodes.

12. The sensor array of claim 1, wherein each of said discrete sensor nodes includes a chemical sensor.

13. The sensor array of claim 1, wherein each of said discrete sensor nodes includes an accelerometer.

14. The sensor array of claim 1, wherein each of said discrete sensor nodes includes a piezoceramic sensor.

15. The sensor array of claim 14, wherein said piezoceramic sensor further comprises a plurality of piezoceramic fibers arranged in a planar array in which said piezoceramic fibers are aligned substantially parallel to each other.

16. The sensor array of claim 14, wherein said piezoceramic sensor is a piezoceramic wafer.

17. A sensor, said sensor comprising:
   (a) a plurality of piezoceramic fibers arranged in a planar array in which said fibers are aligned substantially parallel to each other, each of said fibers having a plurality of polarized regions that are substantially oriented according to their polarity; and
   (b) an electrical interface connecting said plurality of polarized regions of each fiber in series with one another.

18. The sensor of claim 17, wherein said electrical interface further includes at least one electrical bus substantially aligned with said fibers.

19. The sensor of claim 17, wherein said plurality of polarized regions are substantially oriented in series with respect to each other.

20. The sensor of claim 17, wherein said plurality of polarized regions are substantially oriented in parallel with respect to each other.

21. The sensor of claim 17, wherein a first portion of said plurality of polarized regions are substantially oriented in parallel with respect to each other and a second portion of said plurality of said plurality of polarized regions are oreineted in series with respect to each other.

22. A sensor array for nondestructively monitoring a structure to detect a critical event, said sensor array comprising:
   (a) a plurality of discrete sensor nodes, each of said discrete sensor nodes producing an electrical signal in response to a structural event, said sensor nodes including a plurality of piezoceramic fibers arranged in a planar array in which said fibers are aligned substantially parallel to each other, each of said fibers having a plurality of polarized regions that are substantially oriented according to their polarity; and an electrical interface connecting said plurality of polarized regions of each fiber in series with one another;
   (b) a signal adder for receiving and combining said electrical signals from each of said discrete sensor nodes to form a single sensor array output signal; and (c) a signal processing module for receiving and processing said single sensor output signal.

23. The sensor array of claim 22, wherein said signal processing module includes an input connected to said signal adder, an impedance matching amplifier connected to said input for amplifying said single sensor output signal, and an output.

24. The sensor array of claim 23, further including an electronic trigger for detecting the beginning of an event and providing a trigger signal.

25. The sensor array of claim 24, further including a display connected to said trigger and to said output, whereby said tigger signal activates said display for observing said output.

26. The sensor array of claim 25, wherein said display is an oscilloscope.

27. The sensor array of claim 23, further including a threshold detector for detecting an output exceeding a predetermined threshold level and providing an alarm signal.

28. The sensor array of claim 27, further including an alarm connected to said threshold detector whereby said alarm is actuated when said output exceeds said predetermined threshold level.

29. The sensor array of claim 23, wherein said signal processing module further includes an electronic noise filter.

30. The sensor array of claim 22, wherein said plurality of discrete sensor nodes is further divided into discrete subgroups, each located at a different structural location.

31. The sensor array of claim 22, wherein said electrical interface further includes at least one electrical bus substantially aligned with said fibers.

32. The sensor array of claim 22, wherein said plurality of polarized regions are substantially oriented in series with respect to each other.

33. The sensor array of claim 22, wherein said plurality of polarized regions are substantially oriented in parallel with respect to each other.

34. The sensor array of claim 22, wherein a first portion of said plurality of polarized regions are substantially oriented in parallel with respect to each other and a second portion of said plurality of said plurality of polarized regions are oriented in series with respect to each other.

35. A method for monitoring the health of a structure, said method comprising the steps of:

(a) detecting a structural event at a plurality of discrete sensor nodes;

(b) producing an electrical signal in each of said discrete sensor nodes in response to the structural event; and (c) receiving and combining said electrical signal from each of said discrete sensor nodes; and (d) forming a single sensor array output signal corresponding to said structural event.

* * * * *